United States Patent [19]

Dellacorna et al.

[11] Patent Number: 5,233,999
[45] Date of Patent: Aug. 10, 1993

[54] ELECTROMYOGRAPH WITH DATA TRANSMISSION COMPRISING NO METALLIC CONDUCTORS

[75] Inventor: Alberto Dellacorna, Cisliano, Italy
[73] Assignee: B.T.S. Bioingegneria Tecnologia e Sistemi S.r.l., Milan, Italy
[21] Appl. No.: 819,350
[22] Filed: Dec. 26, 1991

[30] Foreign Application Priority Data

Dec. 28, 1990 [IT] Italy .............................. 22566 A/90

[51] Int. Cl.⁵ .............................................. A61B 5/04
[52] U.S. Cl. ................................................ 128/733
[58] Field of Search ................ 128/733, 774, 782, 903

[56] References Cited

U.S. PATENT DOCUMENTS

| | | | |
|---|---|---|---|
| 3,905,355 | 9/1975 | Brudny | 128/733 |
| 4,170,225 | 10/1979 | Criglar et al. | 128/733 |
| 4,537,200 | 8/1985 | Widrow | 128/696 |
| 4,540,000 | 9/1985 | Doherty et al. | 128/696 |
| 4,709,704 | 12/1987 | Lukasiewicz | 128/644 |
| 4,785,813 | 11/1988 | Petrofsky | 128/733 |
| 4,807,642 | 2/1989 | Brown | 128/733 |
| 4,811,742 | 3/1989 | Hassel et al. | 128/733 |

FOREIGN PATENT DOCUMENTS 0059172 9/1982 European Pat. Off. .
WO90/11049 10/1990 World Int. Prop. O. .

OTHER PUBLICATIONS

"Hybrid amplifier-electrode module for measuring surface electromyographic potentials", *Medical and Biological Engineering and Computing*, vol. 18, No. 1, Jan. 1980, by Van Der Locht et al., pp. 119-122.

Primary Examiner—Max Hindenburg
Attorney, Agent, or Firm—Young & Thompson

[57] ABSTRACT

An electromyograph includes a patient portable unit to pick up data derived by detecting electrodes and to transmit them to a fixed base unit which receives the data, processes them further, and makes them available to a known reading unit. The signals between the two units are exchanged in digital form through at least one optical fiber cable or a radio communication device, which allows a wide freedom of movement to the patient and guarantees absolute electric insulation.

17 Claims, 4 Drawing Sheets

ELECTROMYOGRAPH WITH DATA TRANSMISSION COMPRISING NO METALLIC CONDUCTORS

BACKGROUND OF THE INVENTION

1. Field of the Invention

The present invention concerns an electromyograph wherein the data detected on the patient is transmitted to the receiving unit without the use of metallic conductors, for instance by optical means or by radio communication.

The electromyograph is a medical instrument used to detect the electric muscular activity by means of surface electrodes applied on the patient's skin, or by means of needle electrodes inserted into the patient's muscle in the body parts of which the muscular functionality needs to be studied. The instrument is used more and more frequently to study the physiology of the muscular apparatus in healthy subjects and to thus acquire data for use in the study and treatment of muscular pathologies and, in particular, in therapies to recover the muscular functionality of previously injured parts.

2. Description of the Prior Art

The electromyograph of known technique uses the same technology of the already known and tested instruments for detecting the electric activity of other organs of the human body, as for instance the electroencephalograph or the electrocardiograph, and it hence consists of a table instrument from which a plurality of electric cables are connected to electrodes suitably fixed to the patient's body. This technique, which has given and still gives satisfactory results in the study of the heart and brain functions, has instead not given equally satisfactory results in the study of the muscular functions. This technique depends on a variety of factors, all however substantially leading to the fact that the muscular functions have to be measured while the muscle is contracting and thus in a dynamic condition, as opposed to the previously cited functions which can be taken in a fully static condition.

This objective requirement involves in fact some serious drawbacks which have prevented up to date the hoped for wider spreading of electromyographs, and the studies and cognitions connected thereto.

Among these drawbacks, one should remember in the first palce the need to dispose of sufficiently long electric cables, allowing them to follow the patient's movements which are at times particularly outstretched as, for example, in the case of deambulation; the problem is not, in fact, to simply dispose of cables of the required length, but rather to allow the patient to perform sufficiently free and natural movements in spite of the presence of such cables. The actual cable must therefore be kept rolled up on a bobbin and must be unrolled on pulleys up to the point of reaching the patient, whereby it is easily subject to mechanical failures at the points of higher stress.

A second serious problem concerns the patient's protection against electric shocks; the patient is in fact physically connected to the power mains through the electromyograph and the cables connecting the electrodes, i.e. through metallic conductors, insulation being guaranteed only by the presence of suitable electronic insulating devices allowing to transmit the electric signals but not the electric current, for instance by interrupting the metallic conductors through electric optical devices. Such insulating devices may however be subject to failures or damage, whereby there is always the danger of current leakages between the main circuit and the electric circuit detecting the signal and contacting the patient. The laws providing for safety measures on such instruments are hence becoming stricter and stricter, thereby involving high construction costs, especially when the instruments have also to be used —as in the present case— in dynamic conditions, which objectively increase the possibilities of accidental damages.

A third drawback is tied to the fact that the electric activity at muscular level is very feeble and thus must to be considerably amplified so as to be perceived by the instruments. The electric interferences which may overlap the signals coming from the muscular activity, and consequently modify them, are therefore particularly troublesome; these no doubt include the interferences generated by the movement of the electric cables connecting the electrodes to the instrument within the electromagnetic fields existing in the environment, and those deriving from the impedance variations of the electrode/patient interface.

The object of the present invention is to thus supply an electromyograph apt to overcome all the above mentioned drawbacks, allowing the patient to be constantly and perfectly insulated from the main electric circuit, allowing him a wide freedom of movement, and finally eliminating the electric interferences determined by the movement of the metallic cables transmitting the electric signals.

SUMMARY OF THE INVENTION

According to the present invention, said object is reached by means of an electromyograph, of the type in which the electric muscular activity is detected by means of electrodes applied on the skin or inserted into the patient's muscle, characterized in that it comprises a portable unit applied on the patient and electrically connected to said electrodes, apt to pick up the analog signals issued therefrom, to convert them into digital signals and to format them in serial form; transmission means, comprising no metallic conductors, apt to transmit said digital signals formatted in serial form; and a fixed unit connected to said transmission means, apt to receive said formatted and serialized digital signals, and to decode and convert them into analog signals.

According to a first embodiment of the present invention, said transmission means consists of at least one optical fiber cable. According to a second embodiment of the present invention, said transmission means consist of radio communication means.

BRIEF DESCRIPTION OF THE DRAWINGS

The invention will now be described more in detail, with reference to the first embodiment thereof, illustrated by way of example on the accompanying drawings, in which.

DESCRIPTION OF THE PREFERRED EMBODIMENTS

The electromyograph of the present invention faces in an innovating way the problem of detecting the electric muscular activity, thanks to the fact that it substantially comprises two distinct units, reciprocally connected by transmission means comprising no metallic conductors, apt to transmit serialized digital signals; said transmission means consist of optical means or, alternatively, of radio communication means.

A portable unit, light and of small dimensions, is applied on the patient during the test, for instance by simply inserting it into a pocket of his clothes, or by fixing it with belts or other systems to the patient's body if he is wearing no clothes. Detection electrodes are electrically connected to said unit and fixed, thanks to their adhesive surface, into the body parts being tested. Since the signal of the muscular activity is taken in a differential way, each electrode actually consists of a pair of electrodes, whose differential signal is preamplified by a subminiature preamplifier positioned close to the end of the electrode cable, preferably at a distance of not more than 20 mm from the pair of electrodes, so as to render completely negligible the electric interferences determined by the movement of the cables. The portable unit picks up the signals issued from the electrodes and filters them, then provides for their A/D conversion and finally formats them in serial form. This unit allows the operator to use the transmission means without metallic conductors of the present invention for transmitting the digital serialized signals to a fixed remote unit in an easy and interference-free way.

Said fixed remote unit decodes the digital serialized signals received from the portable unit through said transmission means, then provides for the D/A reconversion thereof, thereafter amplifies and filters them, and finally makes avialable to the operator the processed signals. The fundamental parameters of the signals, for each detection channel, can be regulated to the operator. A digital output is provided, as an alternative to the analog output, in the event of the signals having to be further processed by a data processor.

Figure 1:
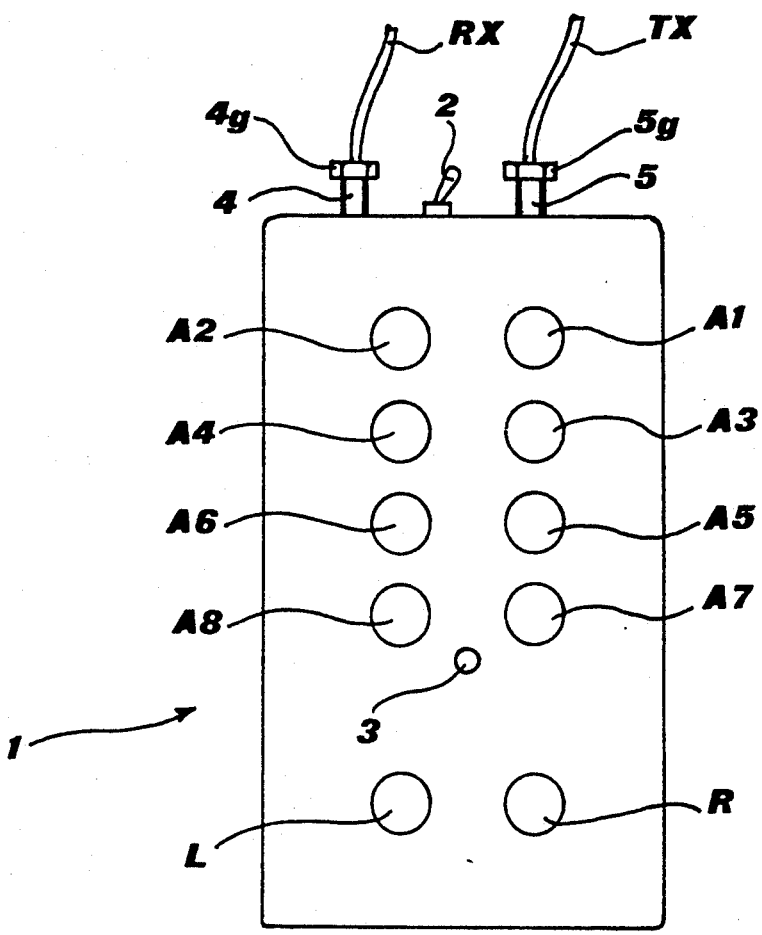
FIG. 1 is a diagrammatic elevation view of the portable unit of the electromyograph according to the present invention.

FIG. 1 shows the portable unit 1 of the electromyograph, carrying on the front panelboard ten connectors, and precisely the connectors A1-A8 designed to connect an equal number of detection electrodes, and the connectors L and R designed to connect the stride-phase channels of the left and, respectively, right foot. The movements of the foot are registered through the stride-phase channels, by reading the signals issued from three piezo-resistive sensors positioned respectively under the toe, the center and the heel of each foot. Each stride-phase channel hence actually comprises three independent sub-channels.

The portable unit 1 is operated by means of the switch 2 and its working condition is signalled by the warning light 3. The power required to operate the unit 1 is supplied by a 9 V alkaline battery 10 (FIG. 2) housed inside said unit. Two hollow and externally threaded connectors 4 and 5 are finally provided for connection to the fixed unit, into which connectors there are inserted respective optical fiber cables RX and TX which are then fixed in position by tightening the ring nuts 4g and 5g. Naturally, the connectors 4 and 5 may be different from these disclosed above, depending from the optical fiber cable used; for instance fast plug-in connectors are preferred in many applications.

Figure 2:
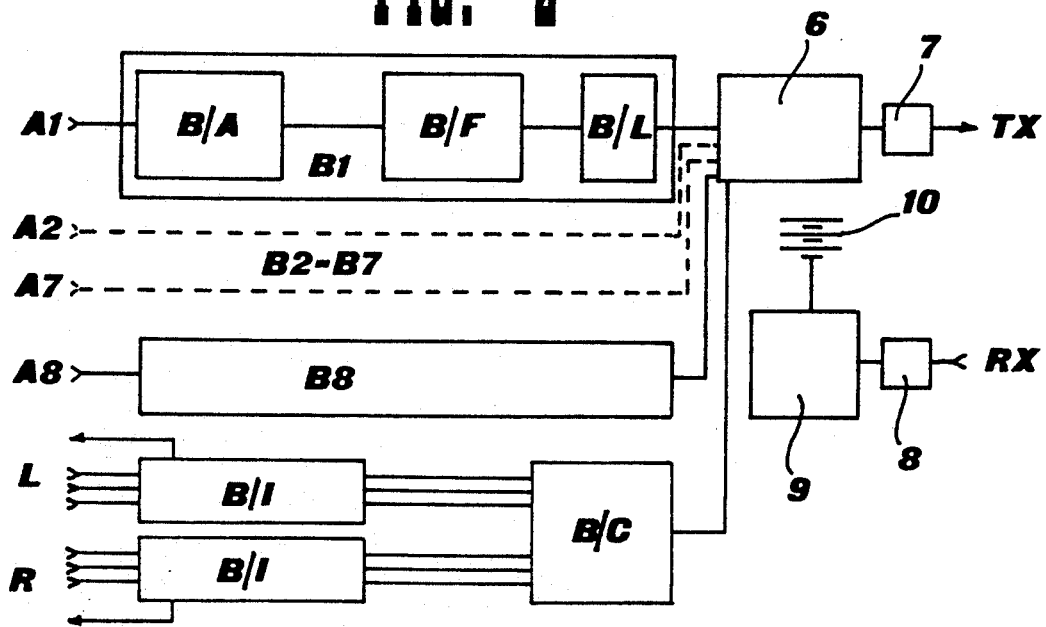
FIG. 2 is a block diagram illustrating the circuitry of the portable unit of FIG. 1.

The block diagram of FIG. 2 shows the circuitry of the portable unit 1. The electric signal issued from the detection electrodes is sent, through the connectors A1-A8, to an equal number of corresponding identical blocks B1-B8, of which only the block B1 is illustrated in further detail for simplicity's sake. The signal issued from the preamplifier of the electrode connected to the connector A1 is thus first of all amplified in stage B/A, realizing a common mode rejection ratio (CMRR) exceeding 100 db. The differential gain of this stage depends on the type of electrode which has been connected, and can be varied by moving a suitable jumper provided in the connector of said electrode or on the printed circuit board of the same stage B/A.

The electrodes are of the standard type ($G=100$) or of the type for reflexology ($G=10$), with input dynamics of 5 mV pp and, respectively, of 50 mV pp. One of the electrodes of the electromyograph according to the present invention comprises, in addition to the pair of detection electrodes, also a third ground electrode apt to supply a reference voltage for all the amplifiers.

The signal thus amplified passes through an anti-aliasing filter B/F with a cutoff frequency of 800 Hz (at $-3$ db) and an attenuation slope of 9 db/octave. Said filter, in order to guarantee a linear in-phase response, is realized with a discrete time oversampling technique, better described hereinafter. An amplifying and voltage limiting stage B/L finally sends the signal to an analog/digital converter 6 which, besides converting the signals into digital form, also formats them in serial form on 10 bit in 200 $\mu$s. The digital signals, thus serialized, are finally transmitted onto the optical fiber cable TX through a transmitting device 7 which receives the signals from the converter 6. The optical transmission is of the asynchronous type with nonstandard protocol.

The portable unit 1 also comprises—as said above—the connectors L and R, which receive the stride-phase signals issued from six piezo-resistive sensors fixed into suitable points, three for each foot of the patient. The signals issued from said piezo-resistive sensors are first sent to an input match stage B/I, where they are compared with a fixed threshold to give an OFF/ON output, and then to a digital/analog converter B/C which generates voltages of variable amplitude according to the state of the piezo-resistive sensors. These analog voltages are sent to the analog/digital converter 6 and are transmitted, similarly to the electromyographic signals, onto a single channel reserved for them, which hence forms the ninth channel of the electromyograph described herein.

The portable unit 1 finally comprises a receiving device 8, connected to a second optical fiber cable RX, through which it is possible to control, directly from the fixed unit, the operation of a supply block 9. This operation in fact allows one to realize—as a result of suitable signals issued from the fixed unit through the optical fiber cable RX—the stand-by condition of the portable unit 1, when this latter unit is not actually in use, thereby increasing the useful life of the battery 10 and thus the working autonomy of said unit 1 (power saving function). The supply block 9 generates the voltages required for the working of the different circuits and for their stabilization, using up the electric energy received from the battery 10.

Figure 3:
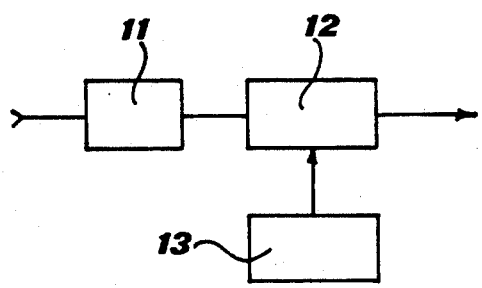
FIG. 3 is a block diagram illustrating the circuitry of one of the channel anti-aliasing filters B/F of the portable unit.
Figure 4:
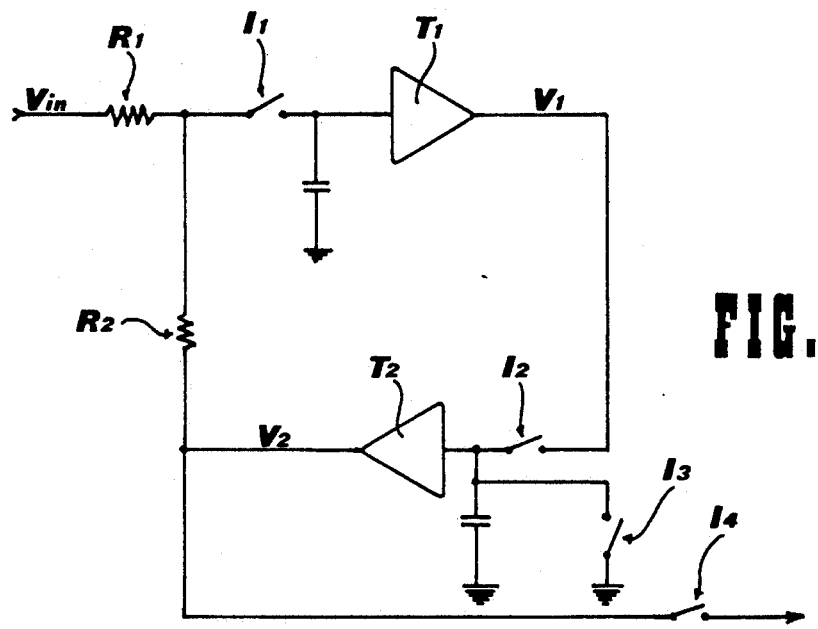
FIG. 4 is a circuit diagram of the moving average filter shown in FIG. 3.
Figure 5:
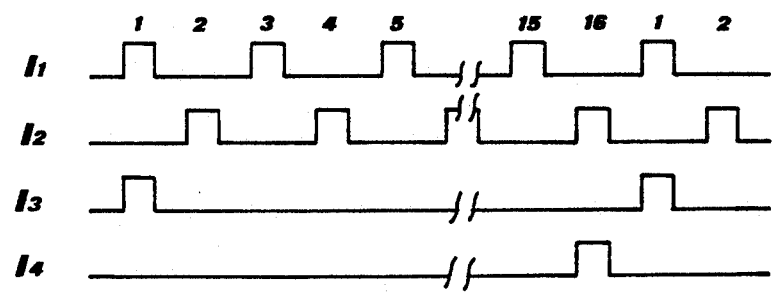
FIG. 5 illustrates the timing cycle of the moving average filter of FIG. 4.

As said above, the anti-aliasing filter B/F-in order to guarantee a linear in-phase response—operates according to a discrete time oversampling technique, which is now illustrated in detail with reference to FIGS. 3 to 7. Said filter is referred to as a discrete time filter in that it operates with a discrete series of measurements taken—as already seen—on an analog signal. The circuitry of one of the anti-aliasing filters B/F is illustrated in FIG. 3, where it can be seen how the input signal is first filtered in a low-pass filter 11, and then in a moving average filter 12 monitored by a monitoring circuit 13. The filter 11 is an RC filter of the first order, which cuts off all the signal components having a frequency higher than FS/2, where FS is the frequency of the first sampling (or oversampling, taken upstream of the filter 12) equal to 40,000 Hz in the illustrated example, in turn equal to eight times the actual sampling frequency FC (downstream of the filter 12) equal to 5,000 Hz. In other words, the signal is sampled with an FS frequency and, on every eight samples thus taken, a moving average filtering operation is carried out in the filter 12, giving rise to a single sample which is supplied at the sampling frequency FC. The circuit of the filter 12 is illustrated in FIG. 4 and its timing cycle in FIG. 5. The cycle starts at time 1 with the closing of the switch $I_3$ which determines the zerosetting of voltage $V_2$ connecting the circuit to earth. At the same time 1, the switch $I_1$ is closed, and the voltage $V_1$ becomes equal to the value $(V_{in(1)}+V_2)/2=V_{in(1)}/2$, thanks to the presence of the divider $R_1-R_2$, which halves the value of the input voltage, and to the amplifier $T_1$. At time 2, the switch $I_2$ is closed and, thanks to the presence of the amplifier $T_2$, which doubles the value of the input voltage, $V_2$ becomes equal to $2xV_1$, namely $V_2=V_{in(1)}$. At time 3, the closing of the switch $I_1$ makes $V_1=(V_{in(3)}+V_2)/2$, namely $V_1=(V_{in(3)}+V_{in(1)})/2$. At time 4, the closing of the switch $I_2$ makes $V_2=V_{in(3)}+V_{in(1)}$. In other words, $V_2$ represents the summing up of the input voltage values at times 1 and 3. The cycle likewise continues, with the alternate closing of the switches $I_1$ and $I_2$—as shown in FIG. 5—for sixteen successive times, so as to obtain at the end of the cycle, namely at time 16, $V_2=V_{in(15)}+V_{in(13)}+\ldots V_{in(1)}$. At this same time 16 also the switch $I_4$ is closed, so that the voltage $V_2$ is sent to the output. At the successive time, a new cycle is started, with the closing of the switch $I_3$ and the consequent zerosetting of the voltage $V_2$.

Figure 6:
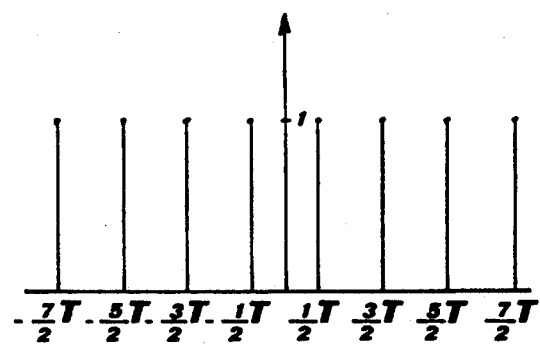
FIG. 6 illustrates the spectrum response of the anti-aliasing filter vs. time.
Figure 7:
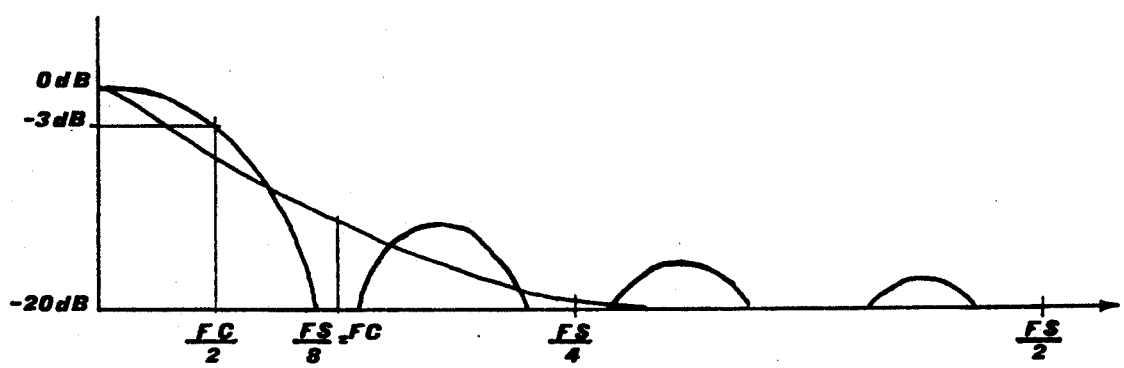
FIG. 7 illustrates the spectrum response of the anti-aliasing filter vs. frequency.

The spectral response of the moving average filter 12 is:

$$F(\omega) = \int_{-\infty}^{+\infty} f(t)e^{j\omega t}dt = 2\sum_{1}^{4} \cos[(2n-1)T/2]$$

and is illustrated, vs. time and vs. frequency, in FIGS. 6 and 7 respectively. In FIG. 6, T represents the oversampling interval, T being $=1/FS$. FIG. 7 reports, as well as the response of filter 12, also the response of the low-pass filter 11. The overall response of the discrete time filter B/F is given by the product of the two functions illustrated in FIG. 7.

The heretofore described portable unit 1 is of extremely limited dimensions and weight; in the embodiment shown, it can in fact be housed to a container of about 15×9×3 cm and it weighs approx. 400 g. Said unit 1 can thus be applied on the patient with extreme easiness and without in the least disturbing or hampering his movements.

Figure 8:
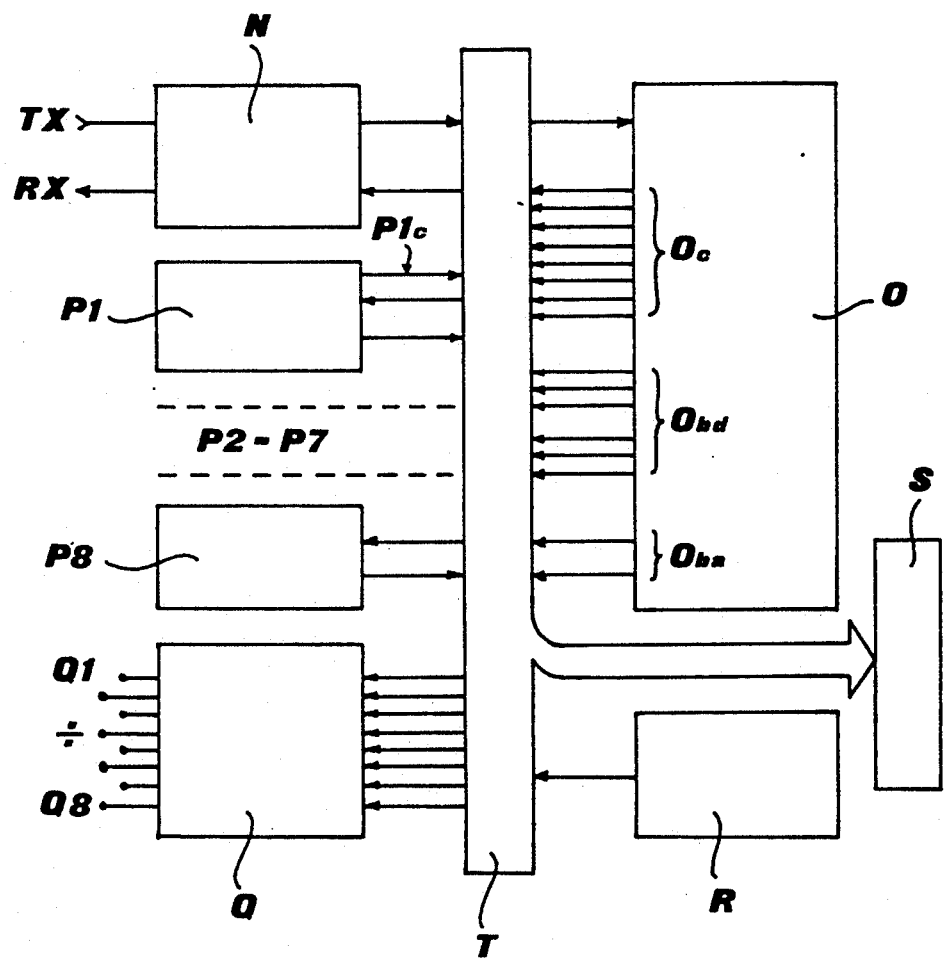
FIG. 8 is a block diagram illustrating the circuitry of the fixed unit of the electromyograph according to the present invention.

The fixed unit of the electromyograph according to the present invention is preferably mounted in a 48.26 cm (19") frame for modular cards in, apt to receive twelve cards Europe format (100×160 mm). The block diagram of this unit is illustrated in FIG. 8.

The signals processed by the portable unit 1 and transmitted by means of the optical fiber cable TX are received into a receiving-transmitting card N. The card N has the double function of converting again into electric signals the optical signals issued from the cable TX and of generating the stand-by optical signal which is transmitted to the receiving device 8 of the portable unit 1 through the cable RX. The digital electric signals issued from the card N are sent, through a single interconnection card T, to a decoding and D/A conversion card O which receives the data sent from the card N in serial form. Each digital string of data contains the sampled values of the eight analog channels, the stride-phase information, the state of charge of the battery and some synchronizing pulses. The card O detects these synchronizing pulses and utilizes the same to carry out the separation of the channels and of the stride-phase information, as well as the 10 bit D/A conversion. The signals relative to the eight electromyographic channels are all made available in Oc to each of the channel filter cards P1-P8, always through the same interconnection card T, so as to be selectively filtered therein, as better explained hereinafter. The stride-phase information on the condition of the six piezo-resistive sensors is instead made directly available on the rear panelboard S of the fixed unit, both in digital form (outputs Obd) and in analog form (outputs Oba).

Each filter card P1-P8 can filter only the signal of one myographic channel, in a way apt to be independently programmed by the operator by means of controls provided on the front panelboard of the fixed unit. Once the filtering operation has been carried out, said signals are sent through the interconnection card T to an output card Q, and are made available for reading through the connectors Q1-Q8 of the BNC type, equally provided on the front panelboard of the fixed unit of the electromyograph according to the present invention.

In addition to the heretofore described analog output, a digital output is provided for the signals which have been decoded in the card O but not yet subjected to digital/analog conversion, and said output is made available on the rear panelboard S of the fixed unit by means of a "D" type 37-pole female cup connector. This output is provided to allow direct processing, by means of an electronic processor, of the detected myographic signals.

The interconnection circuitry of the card T is studied so that the position of the single cards in the frame is totally free. The instrument is thus able to work with a reduced number of cards P, if this should be desirable; since, however, the clock function required for the operation of the cards P is contained in the card P1

(output P1c), it is indispensable for at least this latter card to be constantly inserted into the frame.

The fixed unit is completed by a supply and switching block R, apt to feed said unit, to generate the stabilized voltages required for the operation of the single cards, and to start the stand-by function of the portable unit 1 at the end of the time period in which said unit is allowed to acquire the data. Said time period can be preset at will by the operator or it can be manually started and terminated by the same through appropriate controls provided on the front part of the instrument.

Figure 9:
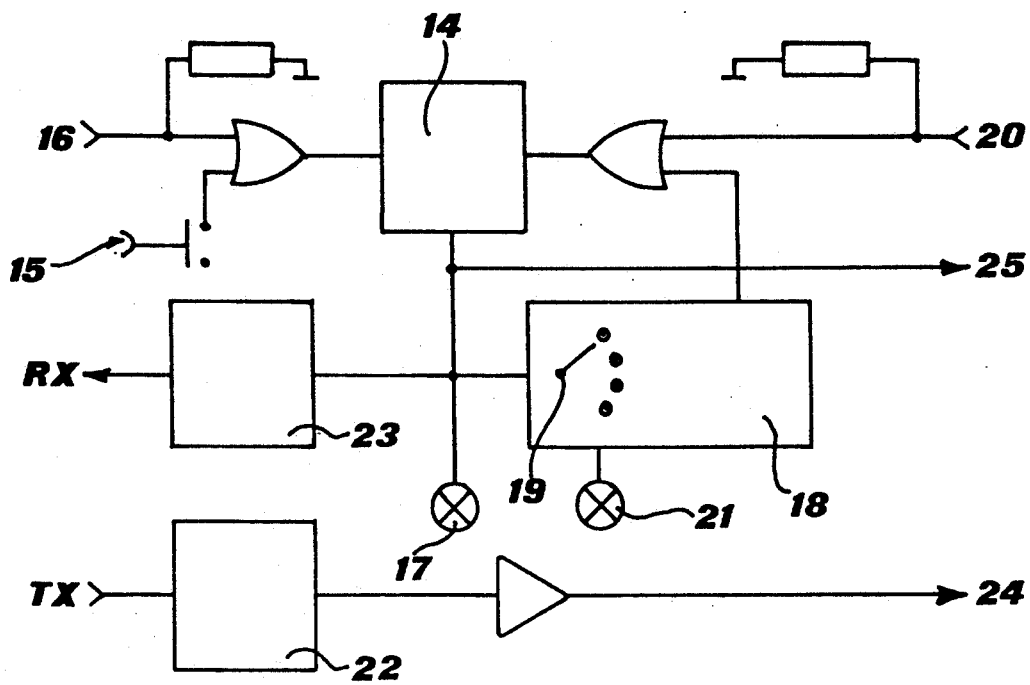
FIG. 9 is a circuit diagram of the receiving and transmitting card N of the fixed unit.

The circuit diagram of the card N is illustrated in further detail in FIG. 9. When the portable unit 1 is operated by means of the switch 2, it can find itself—as said—in two different operating conditions, of data acquisition and respectively of stand-by, in order to optimize consumption of the battery 10 and thus increase its autonomy. The changeover from one to the other of these conditions is controlled by the FLIP/FLOP circuit 14 which is set by the push button 15 or by a remote signal sent to the input 16. The condition of data acquisition is visually signalled by the lighting of the warning light 17.

The FLIP/FLOP circuit 14 is reset—at the end of the operation of data acquisition on the patient—by a timing circuit 18, at the end of the time present by means of the selector 19, or else by means of a remote signal sent to the input 20. In one of its positions, the selector 19 activates the function of manual control of the data acquisition time and it signals said condition by lighting the warning light 21. In this position, the push button 15 takes up a bistable mode and the FLIP/FLOP circuit 14 can thus be set and reset by successively pressing the same button 15.

The card N obviously comprises a receiving device 22, for receipt of the optical signals transmitted by the optical fiber cable TX and for their conversion into digital electric signals, which are sent to the output 24, and a transmitting device 23, connected to the optical fiber cable RX, for the conversion into optical signals of the electric signals sent from the FLIP/FLOP circuit 14. These last signals are made available also to an output 25, for the synchronizing of external devices.

Figure 10:
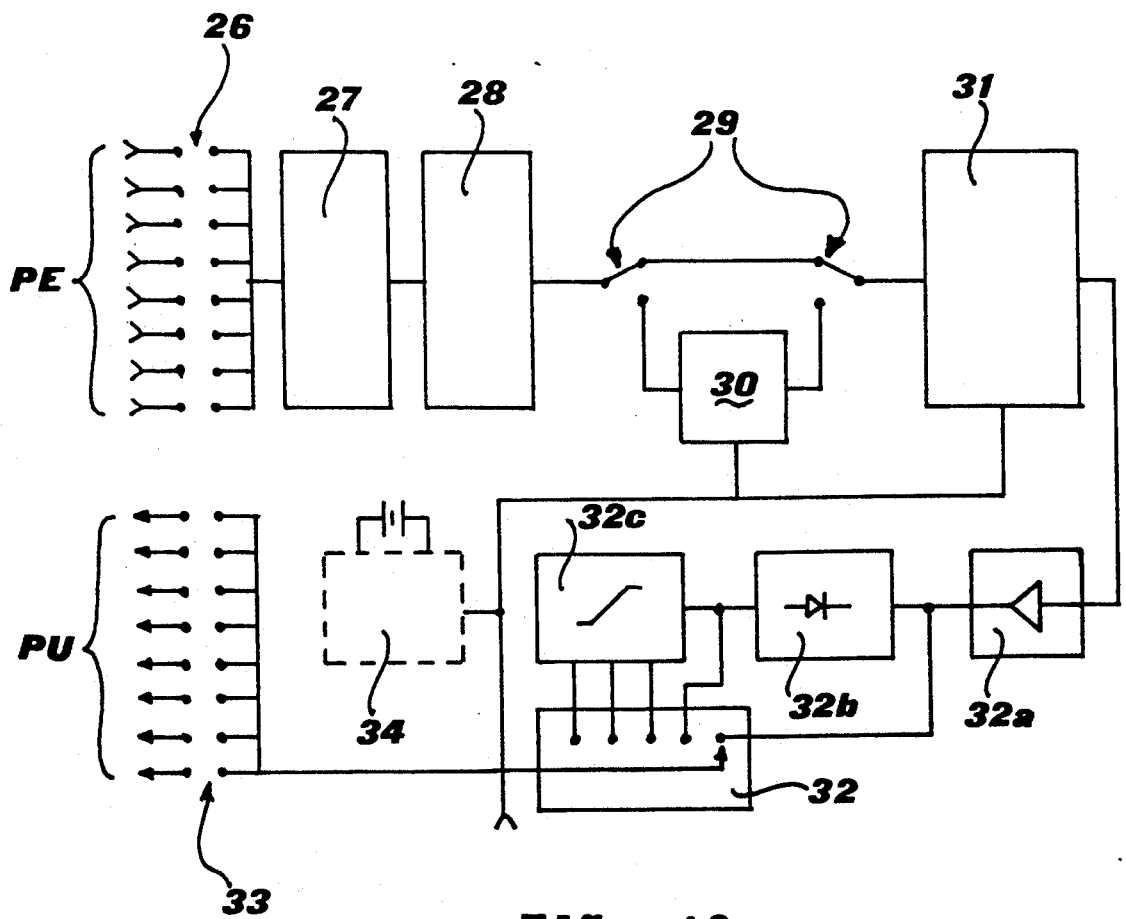
FIG. 10 is a circuit diagram of one of the channel analog filters P1-P8 of the fixed unit.

FIG. 10 illustrates in further detail the circuit diagram of one of the filter cards P1-P8. As already seen further above, the signals from all the eight electromyographic channels are made available on all the cards P, one for each of the eight inputs PE, only one of which is connected to the circuit of the card P by means of a jumper 26. It is hence possible to assign to each card the channel having to be filtered therein by simply inserting the jumper 26 in the corresponding position, whereby the same channel can for example be filtered in more than one card, in different ways.

The electromyographic signal preselected for filtering is first of all sent to a high-pass filter 27, selectable at 1/5/10 Hz, and then to an amplifying stage 28 with selectable gain at 1/2/5/10. An ON/OFF device 29 allows the operator to activate or to exclude the function of a notch filter 30, centred at 50 or 60 Hz for rejecting the interferences from the power mains. The signal then passes onto a low-pass filter 31, which can be selected at 600/400/200 Hz, or totally deactivated in the event one should wish the signal not to be filtered on the high frequencies. An output selector 32 allows the operator to choose between direct output 32a, rectified output 32b, and rectified and integrated output 32c with three different time constants. The signal thus processed is finally sent to eight outputs PU, selectable similarly to the inputs PE by means of a jumper 33.

One of the cards P, and precisely the card P1, also carries a clock oscillator circuit 34, required for the operation of the filters. Said card, as said above, must therefore always be present in the instrument.

In the second embodiment of the electromyograph according to the present invention, the transmission means apt to transmit the digital data between the portable unit and the fixed unit consist—as specified heretofore—of radio communication means.

In particular, the transmitting-receiving devices 7 and 8 of the portable unit shown in FIG. 2, and the receiving-transmitting devices 22 and 23 of the card N of the fixed unit, shown in FIG. 9, are replaced by equivalent radioreceiving-radiotransmitting devices, the construction technology of which is fully known and need not therefore be further illustrated. Obviously, the remaining part of the instrument is perfectly identical to that described heretofore.

I claim:

1. Electromyograph, of the type in which electric muscular activity is detected by electrodes applied on skin or inserted into a patient's muscle, characterized in that it comprises:
   a portable unit applied on the patient and electrically connected to said electrodes, to pick up analog input signals issued therefrom, to convert them into digital signals and to format them in serial form;
   transmission means, having no metallic conductors, to transmit said digital signals formatted in serial form; and
   a fixed unit connected to said transmission means, to receive said formatted and serialized digital signals, and to decode and convert them into analog signals.

2. Electromyograph as in claim 1, wherein the analog input signals in said portable unit from each electrode, are filtered into an anti-aliasing filter before carrying out the analog/digital conversion thereof.

3. Electromyograph as in claim 2, wherein said anti-aliasing filter has a cutoff frequency of 800 Hz (at $-3$ dB) and an attenuation slope of 9 dB/octave.

4. Electromyograph as in claim 2, wherein said anti-aliasing filter includes, in series, a first low-pass filter and a second moving average filter to supply signal samples at a sampling frequency, said samples being an average of signal samples picked up at an oversampling frequency higher than said sampling frequency.

5. Electromyograph as in claim 4, wherein the first low-pass filter is an RC filter of the first order, which cuts off all the signal components having a frequency higher than half the oversampling frequency.

6. Electromyograph as in claim 4, wherein the oversampling frequency is equal to eight times the sampling frequency.

7. Electromyograph as in claim 4, wherein the sampling frequency is equal to 5,000 Hz.

8. Electromyograph as in claim 1, wherein said fixed unit also includes filter devices, distinct for the signals of each electrode, in order to filter the signals after their conversion into analog signals.

9. Electromyograph as in claim 8, wherein each of said filter devices includes, in series, a high-pass filter, a notch filter, and a low-pass filter.

10. Electromyograph as in claim 8, wherein one of said filter devices also includes a clock oscillator circuit.

11. Electromyograph as in claim 8, wherein an output signal from each of said filter devices is rectified, or rectified and integrated.

12. Electromyograph as in claim 1, wherein operation of said portable unit is controlled by said fixed unit by exchange of serialized digital information through said transmission means.

13. Electromyograph as in claim 1, wherein said transmission means consists of at least one optical fiber cable.

14. Electromyograph as in claim 1, wherein said transmission means consist of radio communication means.

15. Electromyograph as in claim 14, wherein one of said electrodes also includes a third earth electrode, to supply a reference voltage.

16. Electromyograph as in claim 1, wherein said portable unit contains an autonomous power supply.

17. Electromyograph as in claim 1, wherein each of said electrodes consists of a pair of differential electrodes, whose signal is amplified by a subminiature preamplifier, positioned at a distance from said electrodes not exceeding 20 mm.

* * * * *